(12) United States Patent
Matschke et al.

(10) Patent No.: US 10,451,298 B2
(45) Date of Patent: Oct. 22, 2019

(54) GERMICIDAL APPARATUS

(71) Applicants: Brett A. Matschke, Trumbull, CT (US); Sean A. Matschke, Botsford, CT (US); Nailen T. Matschke, Trumbull, CT (US)

(72) Inventors: Brett A. Matschke, Trumbull, CT (US); Sean A. Matschke, Botsford, CT (US); Nailen T. Matschke, Trumbull, CT (US)

(*) Notice: Subject to any disclaimer, the term of this patent is extended or adjusted under 35 U.S.C. 154(b) by 93 days.

(21) Appl. No.: 15/525,989

(22) PCT Filed: Nov. 19, 2015

(86) PCT No.: PCT/US2015/061530
§ 371 (c)(1),
(2) Date: May 11, 2017

(87) PCT Pub. No.: WO2016/081703
PCT Pub. Date: May 26, 2016

(65) Prior Publication Data
US 2017/0307234 A1    Oct. 26, 2017

Related U.S. Application Data

(60) Provisional application No. 62/081,651, filed on Nov. 19, 2014.

(51) Int. Cl.
*A61L 2/10* (2006.01)
*F24F 3/16* (2006.01)

(52) U.S. Cl.
CPC ........... *F24F 3/166* (2013.01); *A61L 2/10* (2013.01); *F24F 3/16* (2013.01); *F24F 2003/1667* (2013.01)

(58) Field of Classification Search
CPC ......... A61L 2/10; F24F 3/166; F24F 2003/667
USPC ............... 422/1, 5, 24, 186, 186.3, 306; 250/455.11, 492.1
See application file for complete search history.

(56) References Cited

U.S. PATENT DOCUMENTS

| | | | |
|---|---|---|---|
| 4,011,456 A | 3/1977 | Bredewater et al. | |
| 5,861,633 A | 1/1999 | Mandellos | |
| 6,022,511 A | 2/2000 | Matschke | |
| 6,700,128 B2 | 3/2004 | Matschke | |
| 2002/0088945 A1* | 7/2002 | Matschke | ............... A61L 9/20 250/432 R |
| 2003/0217641 A1 | 11/2003 | Palestro et al. | |
| 2005/0000365 A1 | 1/2005 | Nelsen et al. | |

OTHER PUBLICATIONS

International Search Report and Written Opinion dated Mar. 3, 2016 in corresponding International Application No. PCT/US2015/061530, 19 pages.
2014 Cleanetics UV-Tech Product Catalog, 15 pages.
Environmental Control for Tuberculosis: Basic Upper-Room Ultraviolet Germicidal Irradiation Guidelines for Healthcare Settings (DHHS Publication Mar. 2009), 87 pages.
Reed, The History of Ultraviolet Germicidal Irradiation for Air Disinfection, Public Health Reports, Jan.-Feb. 2010, vol. 125, pp. 15-27.

* cited by examiner

*Primary Examiner* — Monzer R Chorbaji
(74) *Attorney, Agent, or Firm* — Carter, DeLuca & Farrell LLP

(57) ABSTRACT

A germicidal UV chamber cleanses air passing through a duct system, such as a central air system.

8 Claims, 13 Drawing Sheets

GERMICIDAL APPARATUS

CROSS-REFERENCE TO RELATED APPLICATION

This application is a national stage of International Application No. PCT/US2015/061530 filed Nov. 19, 2015, which claims the benefit of and priority to U.S. Provisional Application Ser. No. 62/081,651 filed Nov. 19, 2014, the entire contents of which are incorporated herein by reference.

BACKGROUND

Airborne bacteria or other microorganisms permeate the air we breathe and the water we drink. Some of these microorganisms cause disease. Medical environments, such as hospitals, may contain both a high degree of disease-causing pathogens and highly susceptible, weakened patients who need to be protected from those pathogens. The existence of biological weapons of mass destruction requires protection of command centers, barracks, ships, and other closed environments against such biological agents. Sealed high-rise structures with central air conditioning and heating, through duct systems, need protection from the spread of disease among its occupants and from colonies of microorganisms which may live in the duct and water system. Thus, biologic protection is necessary on the battlefield, in the workplace, in the hospital, and in the home.

While various attempts have been made to place ultraviolet light sources in duct systems to germicidally clean fluids (e.g., gas or liquid) passing through the duct system, there remains room for improvement in the design of germicidal apparatus.

SUMMARY

In one aspect of the present disclosure, a germicidal chamber is provided that includes interconnected truncated spherical segments defining a chamber. The chamber has a longitudinal axis, an upstream inlet opening, and a downstream outlet opening. An ultraviolet light source is positioned within the chamber and a grille is positioned adjacent the upstream inlet opening. The grille includes grille elements, each of which defines a portion of a sphere and has a reflective, concave inner-facing surface that focuses ultraviolet light incident on the grille element to a focal point along the longitudinal axis of the chamber. The focal point of each of the grille elements is at a different location along the longitudinal axis. In embodiments, one or more of the grille elements also includes a convex, outer facing surface, at least a portion of which is provided with a light absorbing material. In embodiments, the reflective, concave inner-facing surface of each grille element is a specular reflective surface. In embodiments, a similar grille is positioned adjacent the downstream outlet opening of the chamber.

In another aspect of the present disclosure, a germicidal chamber includes interconnected truncated spherical segments defining a chamber having an upstream inlet opening and a downstream outlet opening. An ultraviolet light source is suspended within the chamber between an upstream mounting ring and a downstream mounting ring. The upstream mounting ring includes a tapered upstream surface. In embodiments, the upstream mounting ring also includes a tapered downstream surface. In other embodiments, the downstream mounting ring includes at least one of a tapered upstream surface or a tapered downstream surface.

In another aspect of the present disclosure, a germicidal chamber includes interconnected truncated spherical segments each having an inner surface that collectively define a chamber having an upstream inlet opening and a downstream outlet opening. An ultraviolet light source is positioned within the chamber and the inner surface of each of the truncated spherical segments has a diffuse reflective surface. In embodiments, at least one of the truncated spherical segments includes an access panel. In embodiments, at least one of the interconnected truncated spherical segments is truncated by two planes. In embodiments, at least one of the interconnected truncated spherical segments is truncated by two planes oriented at an angle from zero degrees to 90 degrees with respect to each other. In embodiments, at least one of the truncated spherical segments is truncated by two parallel planes. In embodiments, at least one of the interconnected truncated spherical segments is truncated by two planes oriented at 90 degrees with respect to each other. In embodiments, at least one of the interconnected truncated spherical segments is truncated by two planes oriented at 60 degrees with respect to each other. In embodiments, at least one of the interconnected truncated spherical segments is truncated by two planes oriented at 45 degrees with respect to each other. In embodiments, at least one of the interconnected truncated spherical segments is truncated by two planes that meet and are oriented at 60 degrees with respect to each other. In embodiments, at least one of the interconnected truncated spherical segments includes structure for mounting the at least one of the plurality of interconnected truncated spherical segments to a duct of a central air system. In embodiments, the interconnected truncated spherical segments collectively define a chamber that is one of linear, L-shaped, U-shaped or any other shape.

In another aspect of the present disclosure, a kit for making a germicidal chamber is provided and includes a package having a plurality of truncated spherical segments contained therein. The plurality of truncated spherical segments are interconnectable to collectively define a chamber having an upstream inlet opening, and a downstream outlet opening. In embodiments, at least one of the truncated spherical segments contained in the package includes at least one of: an access panel, structure for mounting the at least one of the plurality of interconnected truncated spherical segments to a duct of a central air system, or structure for mounting an ultraviolet light source. In embodiments, at least one of the truncated spherical segments contained in the package has a configuration that is defined by at least one of: truncation by two planes, truncation by two planes oriented at an angle from zero degrees to 90 degrees with respect to each other, truncation by two parallel planes, truncation by two planes oriented at 90 degrees with respect to each other, truncation by two planes oriented at 60 degrees with respect to each other, truncation by two planes oriented at 45 degrees with respect to each other, or truncation by two planes that meet and are oriented at 60 degrees with respect to each other.

BRIEF DESCRIPTION OF THE DRAWINGS

The above and other aspects, features, and advantages of the presently disclosed germicidal apparatus will become more apparent in light of the following detailed description when taken in conjunction with the accompanying drawings in which.

Figure 1:
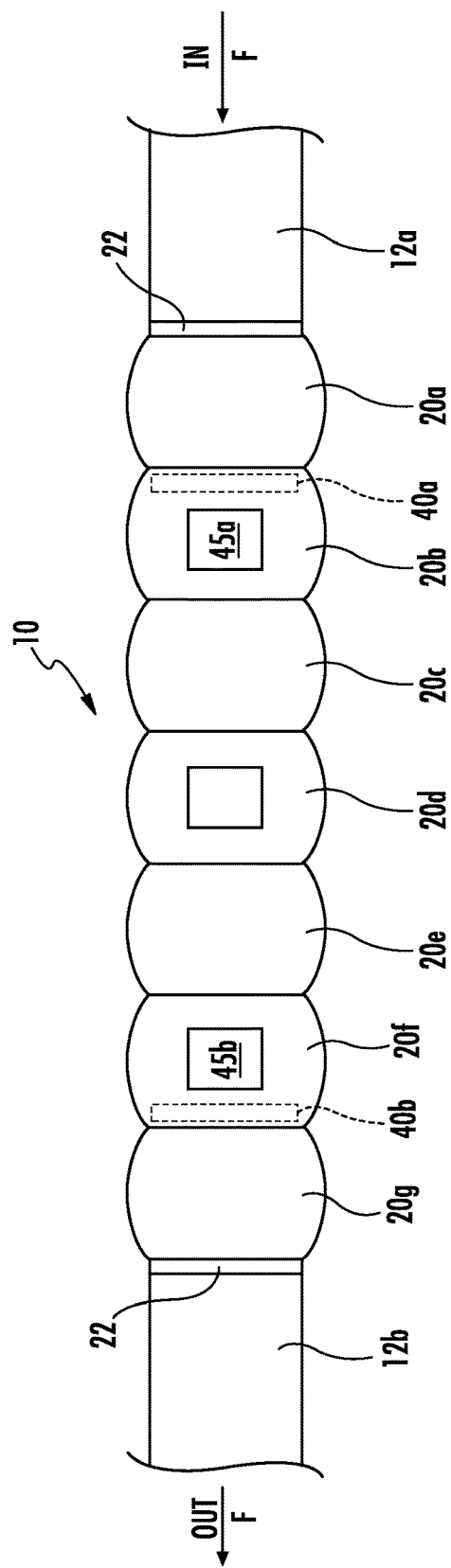
FIG. 1 is a side view of a germicidal chamber in accordance with an exemplary embodiment of the disclosure.

The figures depict specific embodiments for purposes of illustration only. One skilled in the art will readily recognize from the following discussion that alternative embodiments of the structures and methods illustrated herein may be employed without departing from the principles described herein.

DETAILED DESCRIPTION

Particular embodiments are described hereinbelow with reference to the accompanying drawings; however, it is to be understood that the disclosed embodiments are merely exemplary and germicidal apparatus in accordance with the principles described herein may be embodied in various forms. Therefore, specific structural and functional details disclosed herein are not to be interpreted as limiting, but merely as a basis for the claims and as a representative basis for teaching one skilled in the art to variously employ the presently disclosed structures, methods and principles in virtually any appropriately detailed structure.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary." Well-known functions or constructions are not described in detail to avoid obscuring the present disclosure in unnecessary detail. Like reference numerals may refer to similar or identical elements throughout the description of the figures.

As shown in the drawings and described throughout the following description, as is traditional when referring to relative positioning in a dynamic system, the term "upstream" refers to the end of the apparatus at which fluid enters the system and the term "downstream" refers to the end of the apparatus at which fluid exits the system.

In accordance with exemplary embodiments of the present disclosure, the duct work of a central air system is modified to replace a portion thereof with a germicidal cleansing chamber 10 which becomes part of the central air duct system. Germicidal chamber 10 is connected to an air duct 12 and can be mounted to a ceiling by conventional mounting means such as suspension rods, cables or straps (not shown). Air circulated through the central air system by a HVAC fan (not shown), flows from duct 12a, into and through germicidal chamber 10, and then back into duct 12b of the central air system. In embodiments, the volume of the removed duct matches the volume of the chamber replacing it.

Germicidal chamber 10 is made up of a plurality of truncated sphere segments 20a through 20g. While illustrated in the exemplary embodiment of FIG. 1 as including seven segments, it should of course be understood that germicidal chamber 10 may include fewer or more segments. In embodiments, segments 20a-g are individually formed, e.g., molded, stamped or spun, and then joined together. Segments 20a-g may be joined together using any suitable technique. For example, segments 20a-g may include threads at the truncated ends thereof and screw together. As another example, segments 20a-g may include structure at the truncated surfaces that allow the segments to be assembled and held together by a frictional fit. Optionally, an adhesive or welding may assist in keeping segments 20a-g together. In other embodiments, segments 20a-g are collectively, monolithically formed.

Segments 20a-g may be made from spun aluminum or formed from any molded material. The interior surface of segments 20a-g may have reflective properties. Reflective properties may be the result of the material from which segments 20a-g are formed, or may result from a surface treatment or coating applied to the interior surface of segments 20a-g. For example, where segments 20a-g are made from spun aluminum, the characteristics of the spun aluminum may be controlled using techniques within the purview of those skilled in the art to provide a diffuse reflective surface within segments 20a-g. In embodiments, once formed from spun aluminum, the interior of segments 20a-g may be polished or otherwise processed to create a surface that provides specular reflection. In yet other embodiments, where segments 20a-g are made from a relatively non-reflective material, a reflective surface (diffuse or specular) may be provided on the interior surfaces of segments 20a-g by depositing a suitable reflective material (such as, for example, aluminum or other material of a desired reflectiveness) on the interior of segments 20a-g. In embodiments, the reflecting surfaces can be composed of PTFE, ePTFE or a mixture of a binder and reflecting additives such as barium sulfate, magnesium fluoride, magnesium oxide or aluminum oxide, holmium oxide, calcium oxide, lanthanum oxide, germanium oxide, tellurium oxide, europium oxide, erbium oxide, neodymium oxide, samarium oxide or ytterbium oxide. Reflective surfaces may be applied using techniques within the purview of those skilled in the art, such as vacuum depositing, spraying, electrostatic processing or impregnation. It should of course be understood that the interior of segments 20a-g need not be uniformly reflective, but may have different reflectivities.

Where adjacent segments meet, they form an intersection opening sufficient to allow both air and UV irradiation to pass between the segments. In the exemplary embodiment shown in FIG. 1, for example, segments 20a and 20b intersect in a plane at right angle to the principle axis "A" of chamber 10, and the intersection opening is in the form of a circle. In embodiments, the radius of the intersection opening may be equal to or less than 0.16 times the distance of the total chamber length (l) plus the diameter of segment at its widest point (d), i.e., Radius≤0.16 (l+d). The use of an equal-area theorem from the duct-diameter throughout the chamber allows for a constant pressure within the chamber at all times. The constant diameter threshold may be applied whether the intersection opening is a circle, or other shape, and whether the segments are spherical or of any shape other than a sphere. In embodiments, where truncated sphere segments are present, the measurement used in sphere diameter may be about 1.28 times the truncated diameter.

Figure 2:
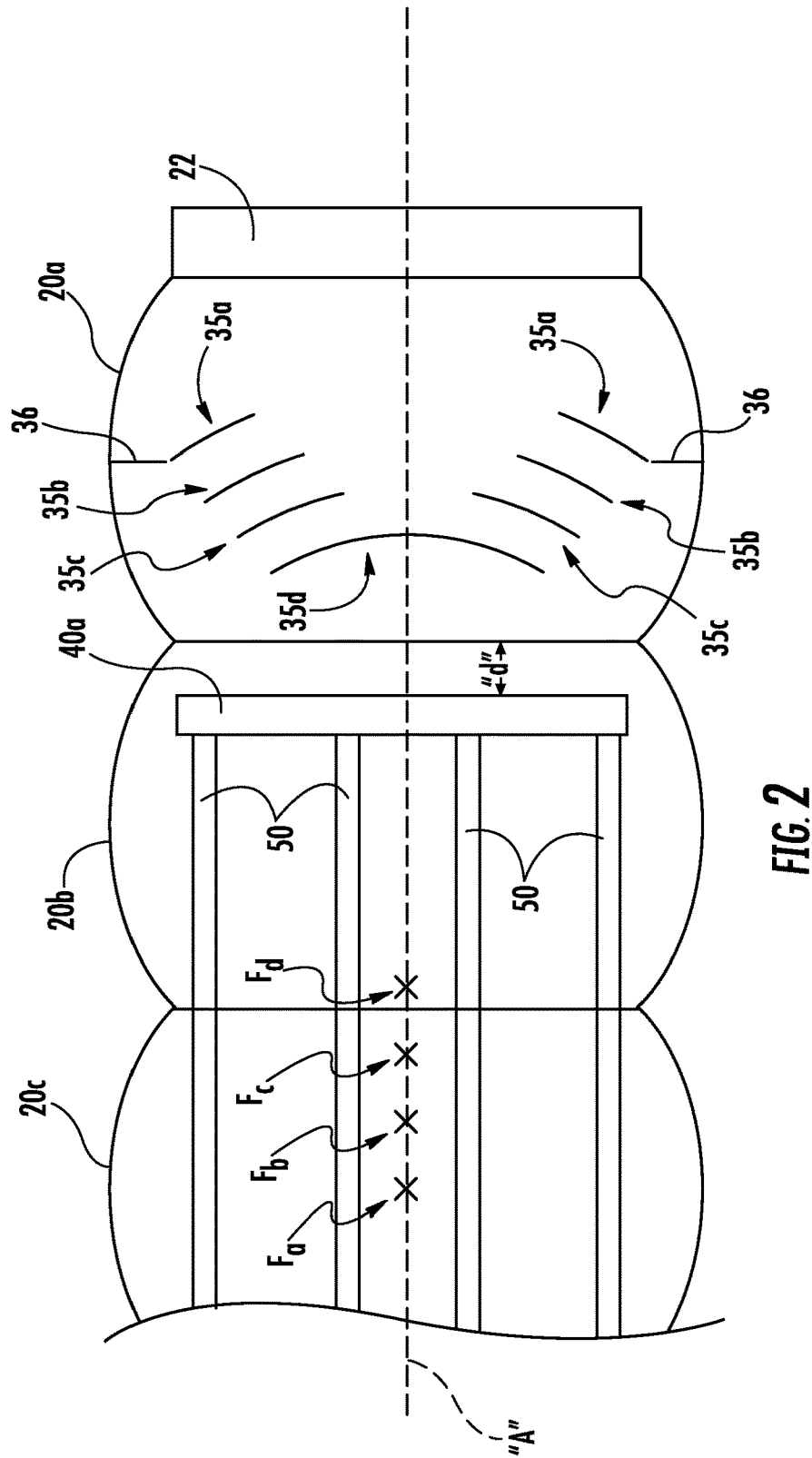
FIG. 2 is a partial cross section of the germicidal chamber of FIG. 1.

The most upstream and downstream segments, segments 20a and 20g in FIG. 1, each includes structure, such as, for example, a collar 22 configured and dimensioned to fit over duct 12a, 12b, for mounting the chamber to a duct of a central air system. Collars 22 on either end of germicidal chamber 10 mate the chamber to the duct system and allow germicidal chamber 10 to be mounted to the duct work of a central air system. Also included within each of segments 20a and 20g is a grille structure 30 (as seen in the exemplary embodiment of FIGS. 2-4) designed to minimize the escape of UV light from germicidal chamber 10.

Figure 3:
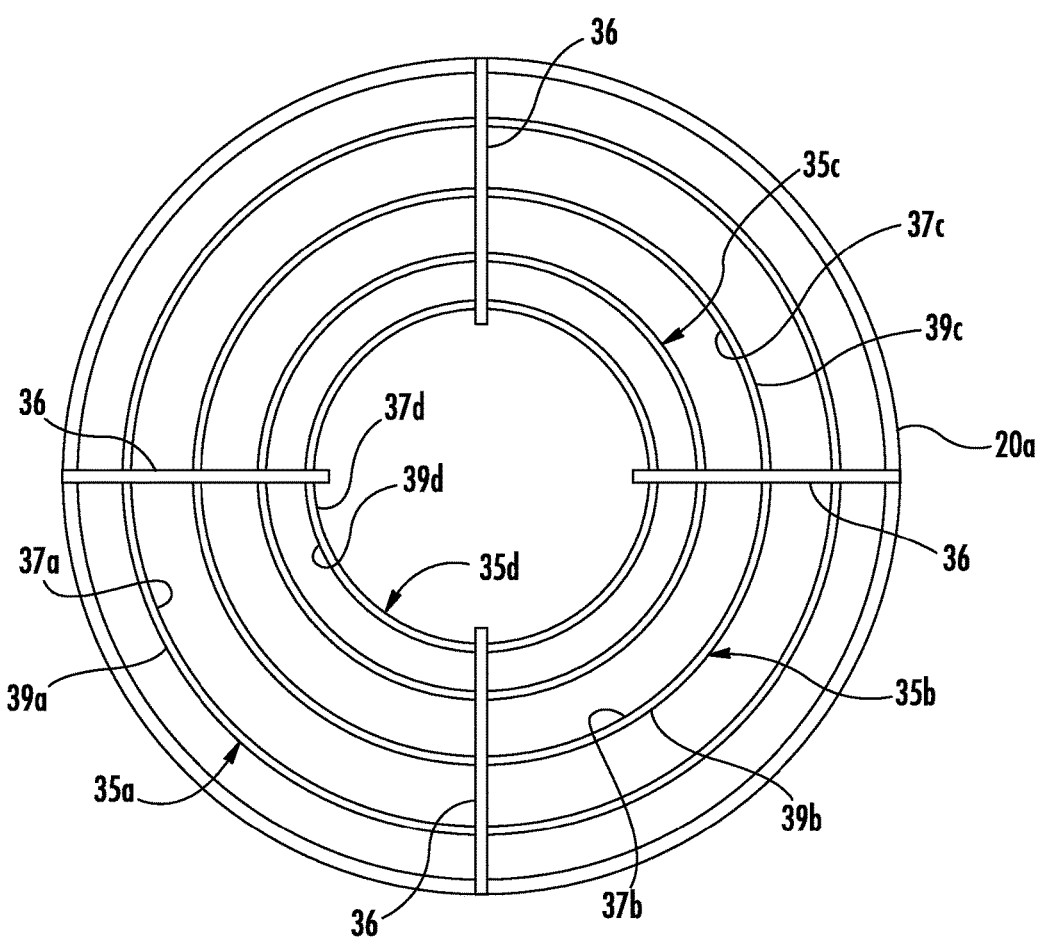
FIG. 3 is a cross section of a grille for use with the germicidal chamber of FIG. 1.
Figure 4:
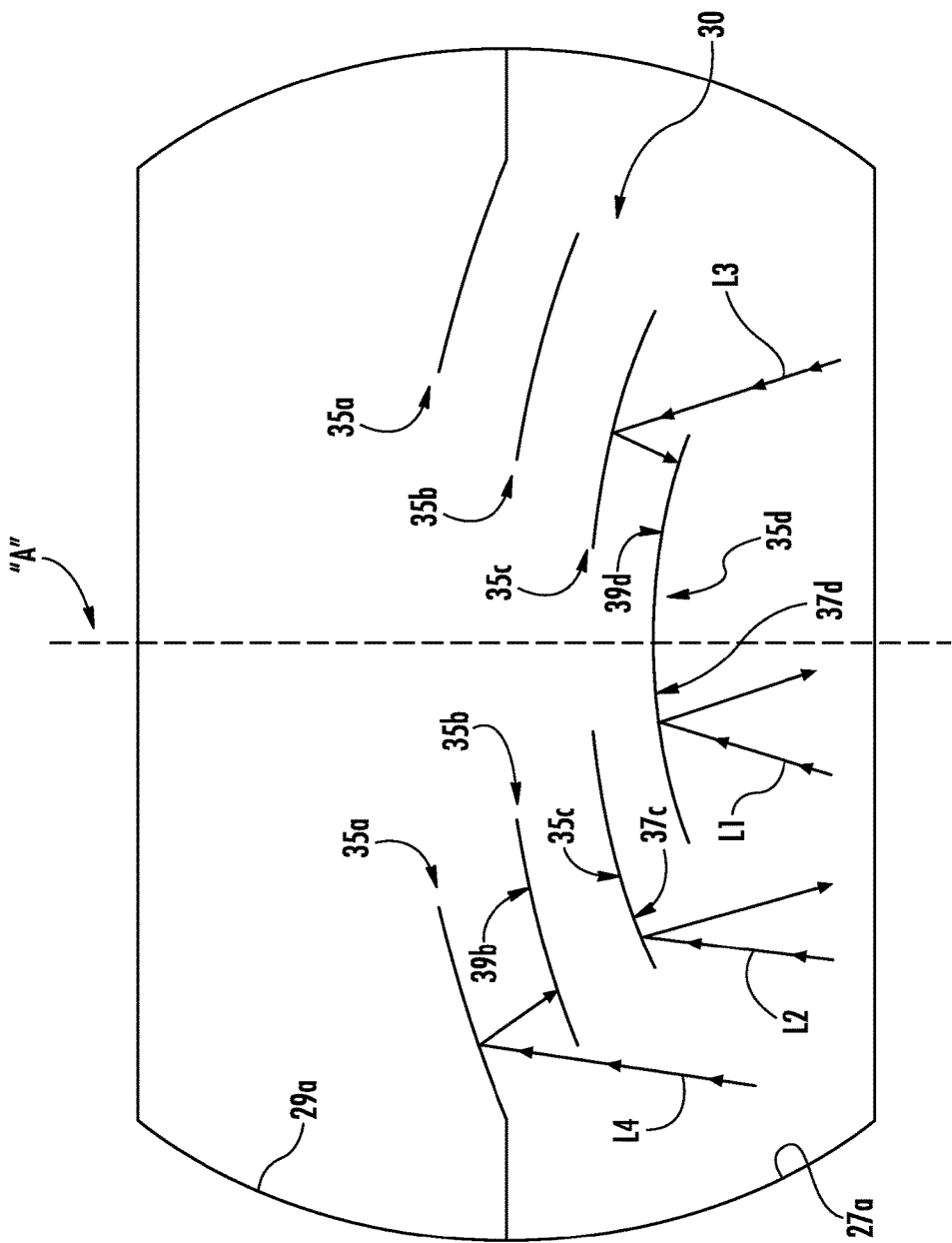
FIG. 4 is a cross section of a segment of the germicidal chamber of FIG. 1 showing light rays reflecting off of the grille.

Grille 30 is formed from a series of truncated spherical grille elements 35a through 35d. Grille elements 35a-d form a series of spatially separated steps having gaps therebetween to allow the passage of air. Grille elements 35a-d are held in place by fins 36 as seen in FIGS. 3 and 4. The number of grille elements, their radial positioning and surface length are a function of the chamber 10 size and the desired air flow. The surface length of each grille element 35a-d generally increases as their diameter and the radial spacing decreases.

Each of grille elements 35a-d includes a reflective, concave inner facing surface 37a-d and a convex, outer facing surface 39a-d, at least a portion of which is provided with a light absorbing material thereon to reduce the reflectivity of light across axis "A". In embodiments, the reflective, concave inner facing surfaces 37a-d are finished to a specular degree reducing diffusion of UV light in segment 20a. The reflective concave inner facing surface of each of grille elements 35a-d focuses light on axis "A", but each of grille elements 35a-d does so at a different focal length. As seen in FIG. 3, light reflected off of grille element 35a will focus light to focal point $F_a$, light reflected off of grille element 35b will focus light to focal point $F_b$, light reflected off of grille element 35c, will focus light to focal point $F_c$, and light reflected off of grille element 35d will focus light to focal point $F_d$.

Grille elements 35a-d act to reflect UV back into the chamber 10. Secondary reflections of UV light occurring between the grille elements 35a-d are either reflected back into the chamber 10 by the reflective, concave inner facing surfaces (see light rays L1 and L2 in FIG. 4), or absorbed by the coating on the convex, outer facing surface of grille elements 35a-d (see light rays L3 and L4 in FIG. 4). Interior surface 29a of segment 20a behind grille 30 may also be coated with a light absorbing material to assist in preventing UV light from being reflected out of germicidal chamber 10. Views into the chamber and thus inadvertent exposure to UV light are blocked by grille 30.

Figure 5A:
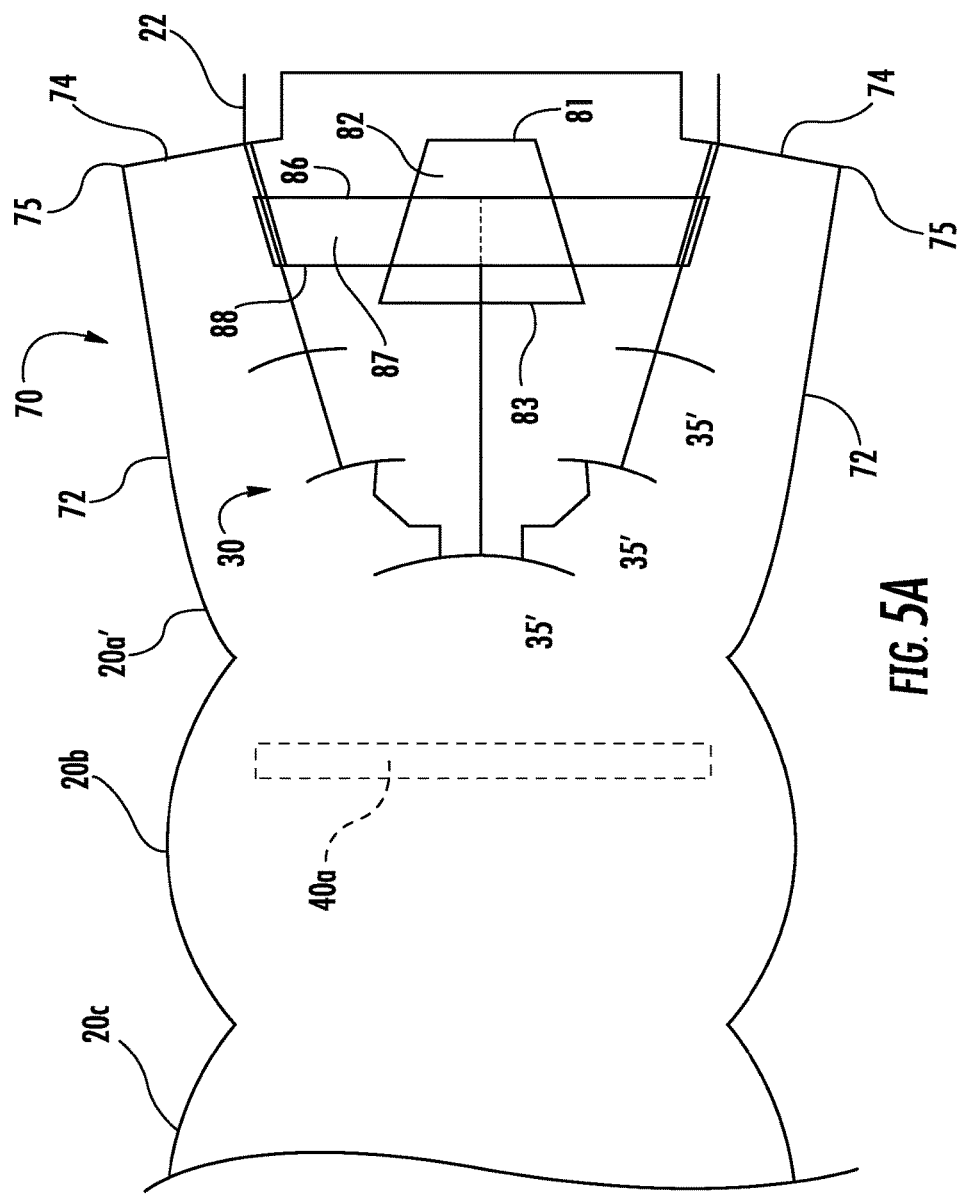
FIG. 5A is a partially cross-sectional side view of a germicidal chamber in accordance with another exemplary embodiment of the disclosure that includes a squared off shell on the upstream-most segment.
Figure 5B:
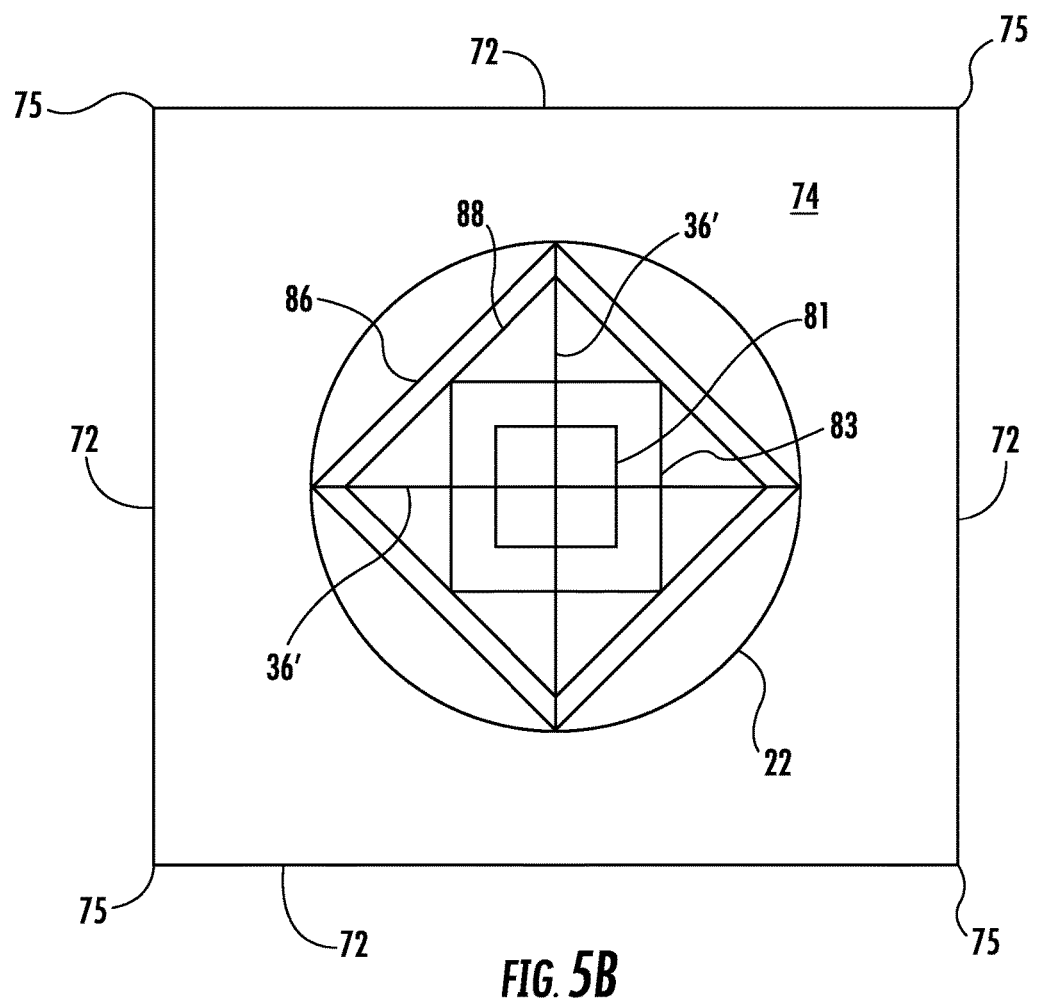
FIG. 5B is an end view of the exemplary embodiment of FIG. 5A, looking into the chamber.

In another exemplary embodiment shown in FIGS. 5A-B, at least one of the most upstream segment or the most downstream segment includes a squared-off shell 70 effective to stop the light energy from escaping the chamber and yet allow for unimpeded airflow. Shell 70, which may be made from ordinary duct aluminum and welded directly to truncated sphere 20a', includes side walls 72 and end wall 74 which meet at corners 75. Corners 75 may be at a right angle as shown in the exemplary embodiment shown in FIGS. 5A-B or may have some other angle. In embodiments, the angle formed at corner 75 may be greater the ninety degrees. The interior of shell 70 is coated with a light absorbing material. Shell 70 terminates in a collar 22 configured and dimensioned to mate the chamber to the duct system as previously described.

Grille structure 30 extends into shell 70 and includes grille elements 35' having characteristics described above designed to minimize the escape of UV light from the germicidal chamber, including a light absorbing material on the convex, outer facing surface of each grille element 35' to reduce the reflectivity of light. Grille elements 35' are supported in place by fins 36'. Fins 36' are oriented at 90-degrees with respect to each other and divide shell 70 into four quadrants. While fins 36' do not reach the side walls 72 of shell 70, they still box up the light energy primarily onto the end wall 74.

Trapezoidal baffles 82, 87 are mounted within shell 70 and also supported by fins 36'. Inner baffle 82 includes upstream edge 81 and downstream edge 83. Outer baffle 87 includes upstream edge 86 and downstream edge 88. The surfaces of baffles 82, 87 are coated with a light absorbing material.

Referring back to FIGS. 1 and 2, segments 20b and 20f of germicidal chamber 10 each includes a mounting ring 40a, 40b between which UV light sources 50 are positioned. Segments 20b and 20f also include access panels 45a, 45b to permit access to mounting rings 40a, 40b and light sources 50 to allow servicing thereof. Four UV light sources 50 are illustrated in the exemplary embodiment of FIG. 2, however it should be understood that the number of UV light sources will be determined by the overall requirements of the system. The exemplary embodiment of FIG. 2 includes an array of linear UV tubes 50. Due to the optic properties of the chamber 10, a UV light source positioned any place in the chamber 10 will result in a uniform distribution of energy throughout the chamber 10 and, thus, the exemplary lamp configuration depicted in the drawings, or any other lamp configuration (e.g., helical lamp configurations as shown in U.S. Pat. No. 6,700,128, the entire contents of which are incorporated herein by this reference), will result in a uniform distribution of light.

In embodiments, mounting ring 40a is positioned within segment 20b, a distance "d" (see FIG. 2) from the upstream end of segment 20b, and mounting ring 40b is positioned within segment 20f a corresponding distance from the downstream end of segment 20f, resulting in less glancing light or reflections directly reaching segments 20a and 20g. Mounting rings 40a, 40b may include sockets (e.g., socket 47 in FIG. 6) to receive UV light sources 50, positioning rods (not shown) to hold the mounting rings 40a, 40b in their respective positions, and an interior circuit board (not shown) protected by the structure of the mounting rings 40a, 40b from UV irradiation. For details of the structure and function of mounting rings 40a, 40b, see U.S. Pat. No. 6,022,511, the entire contents of which are incorporated herein by this reference.

Figure 6:
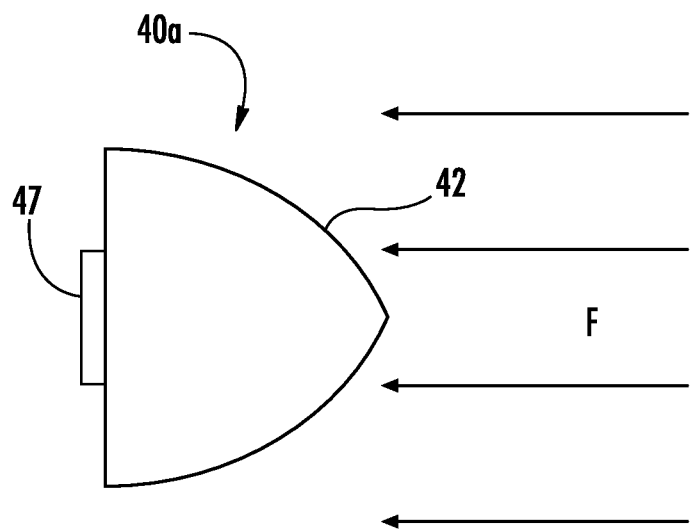
FIG. 6 is a cross section of a mounting ring in accordance with an exemplary embodiment of the disclosure for use with the germicidal chamber of FIG. 1.
Figure 7:
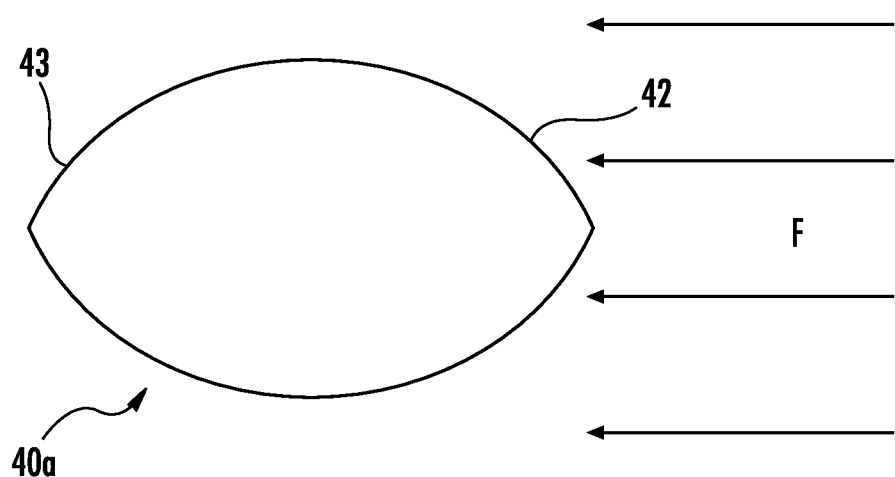
FIG. 7 is a cross section of a mounting ring in accordance with another exemplary embodiment of the disclosure for use with the germicidal chamber of FIG. 1.

In embodiments, mounting ring 40a includes a tapered upstream surface to facilitate air flowing in the direction of arrows "F" over mounting ring 40a as shown in FIG. 6. In other embodiments, both the upstream and downstream surfaces 42, 43 of mounting ring 40a are tapered, giving mounting ring 40a a football shape in cross section as seen in the exemplary embodiment illustrated in FIG. 7. It should, of course, be understood that other mounting rings (e.g., mounting ring 40b) in the chamber may also include tapered surfaces.

Figure 8:
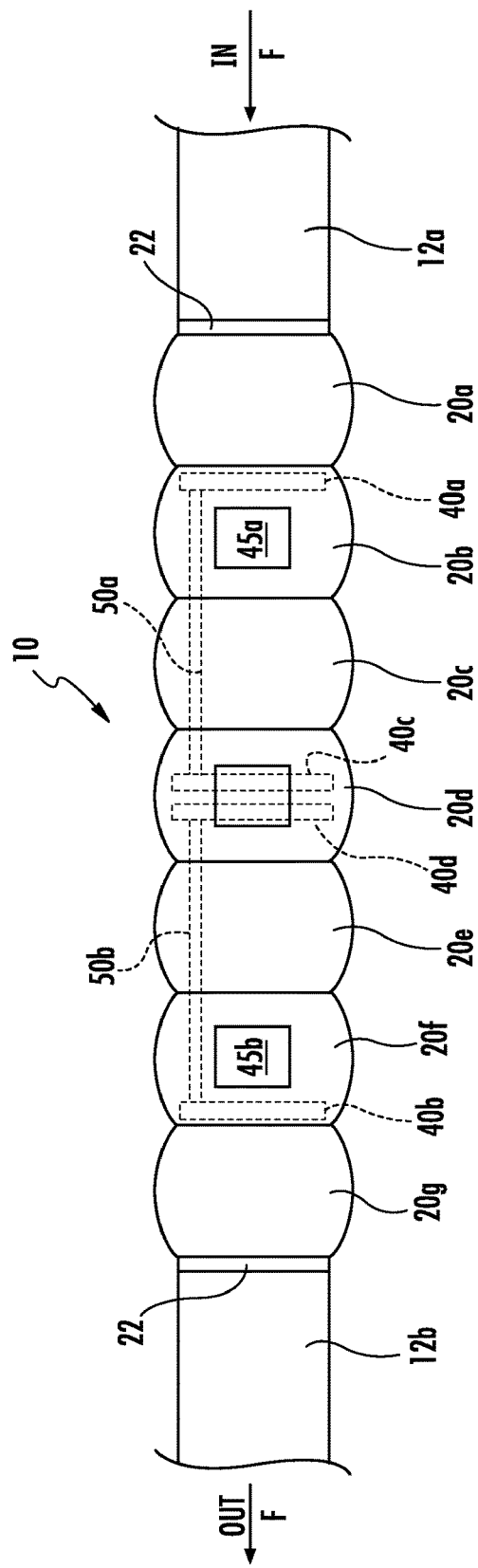
FIG. 8 is a side view of a germicidal chamber in accordance with another exemplary embodiment of the disclosure.

In embodiments where multiple linear UV lamps are provided in an end-to-end arrangement, more than two mounting rings may be provided within the germicidal chamber. An exemplary embodiment is shown in FIG. 8, where UV lamp 50a is positioned between mounting ring 40a in segment 20b and mounting ring 40c in segment 20d, and UV lamp 50b is positioned between mounting ring 40d in segment 20d and mounting ring 40b in segment 20f.

Figure 9:
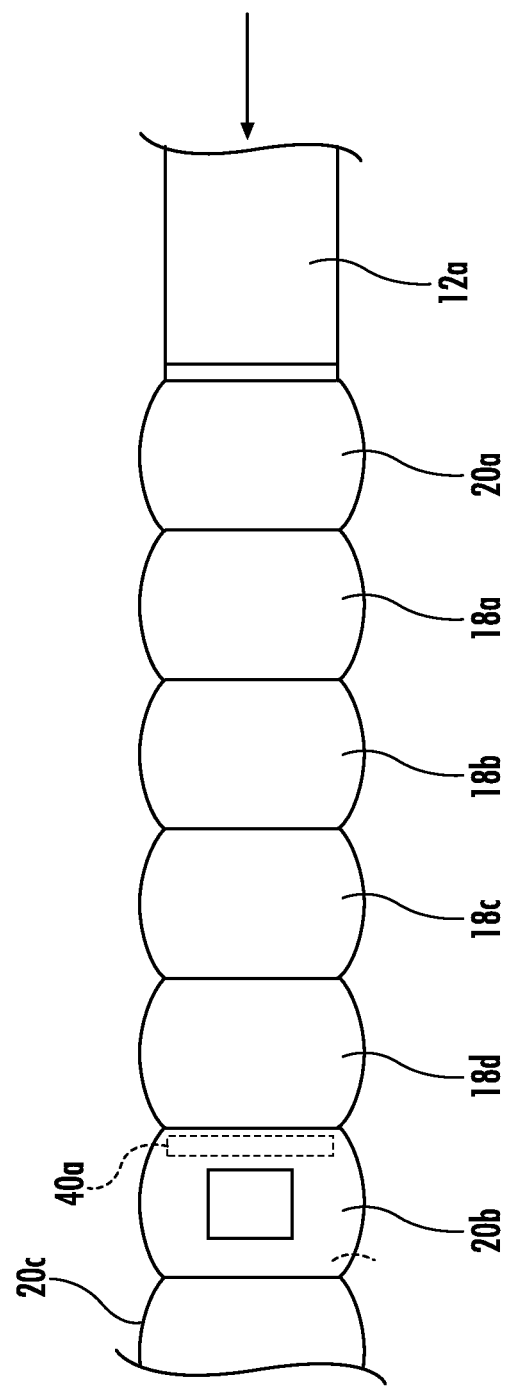
FIG. 9 is a side view of a germicidal chamber in accordance with another exemplary embodiment of the disclosure including "empty" segments.

In embodiments, the chamber includes segments containing no UV light source. Such "empty" segments may be positioned between the segment containing the mounting ring and the duct to which the chamber is attached. One such embodiment is shown in FIG. 9, where segment 20b contains mounting ring 40a, and segments 18a-18d contain no UV light source. While shown with four "empty" segments, it should be understood that any number of "empty" segments may be employed. Additionally, while FIG. 9 shows a chamber with "empty" segments at the upstream end of the chamber, it should be understood that the chamber may also include "empty" segments at the downstream end, or anywhere along the chamber. The number of "empty" segments at each location may be the same or different at each location. Since the entire chamber fills with light essentially instantaneously (at the speed of light), but the air takes a couple seconds to travel the entire length of the chamber, the increased chamber volume resulting from the presence of the "empty" segments provides an increased microbe kill-ratio per pass for the same Watt input, diameter and volumetric flow rate. Because of the spherical configuration of segments 20a-g, UV light generated by the UV light source within germicidal chamber 10 is evenly dispersed throughout the length of germicidal chamber 10. Any point in the germicidal chamber 10 receives the same quantity of UV light in all directions as any other point within the germicidal chamber 10. The formation of the walls of the germicidal chamber 10, by spinning and the qualities of aluminum from which it is spun, acts to ensure the energy generated by the UV light sources 50 is reflected back into germicidal chamber 10 rather than being absorbed by the walls of the chamber. The effect of UV irradiation on a microorganism is dependent on both UV intensity and length of time of exposure to the UV irradiation. Since the interior walls of germicidal chamber 10 are reflective, the irradiation intensity created reaches a steady state which is substantially greater than the output of the lamps and, because of the configuration, is evenly distributed through the chamber. In embodiments, the interior walls of germicidal chamber 10 provide diffuse reflection of UV light, rather than specular reflection of UV light, since a specular reflective surface would create areas of different light intensity, mirroring the effects of the mounting rings and UV light sources, including sockets, wiring, and shadows.

While germicidal chamber 10 is illustrated as being formed from symmetrical truncated spherical sections, it is envisioned that the sections of various, different configurations may be combined to form germicidal chamber 10. For example, it is contemplated that rather than two parallel truncations oriented in a plane at a right angle to the principle axis "A" of the chamber as shown in the exemplary embodiment of FIGS. 1 and 2, the plane of intersection may be at other angles to the principal axis of the chamber. In such cases, the sections could meet at an angle, allowing chamber 10 to be positioned around objects and/or to conform to the available space.

Figure 10:
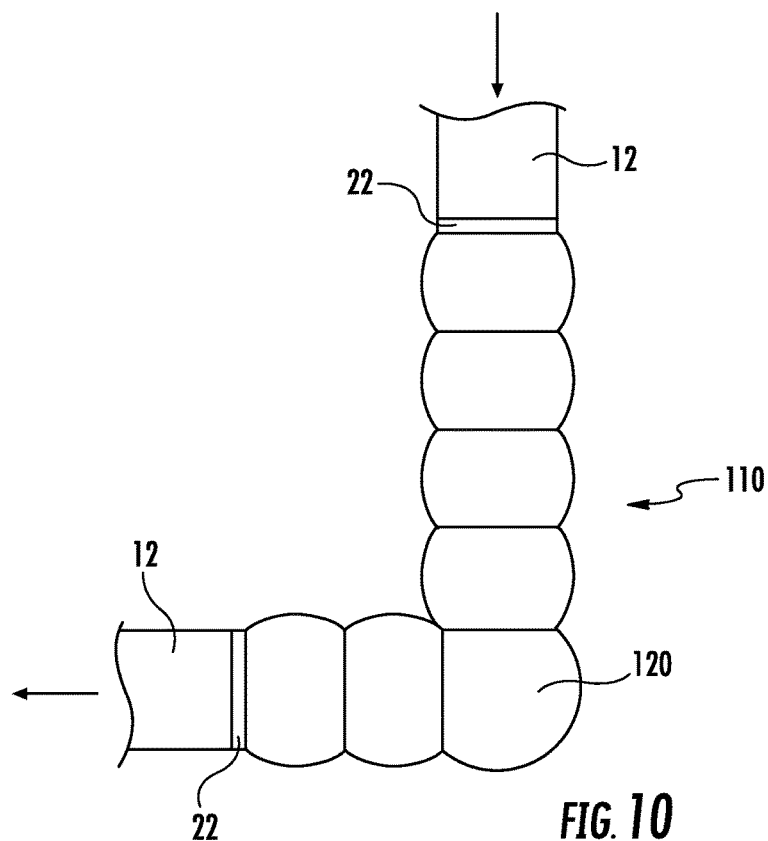
FIG. 10 is a side view of a germicidal chamber in accordance with another exemplary embodiment of the disclosure.
Figure 11:
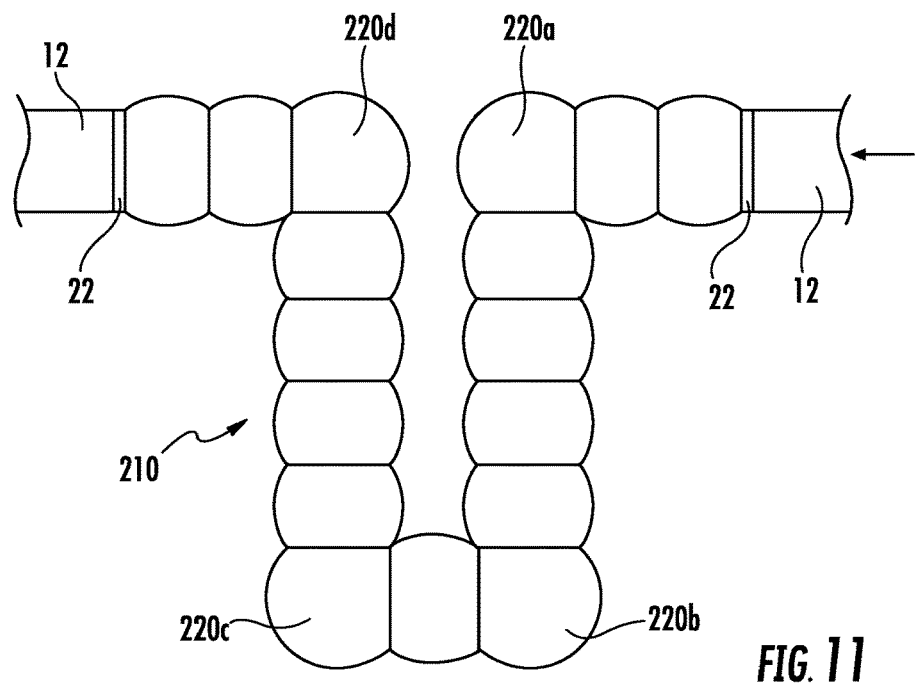
FIG. 11 is a side view of a germicidal chamber in accordance with another exemplary embodiment of the disclosure.
Figure 12:
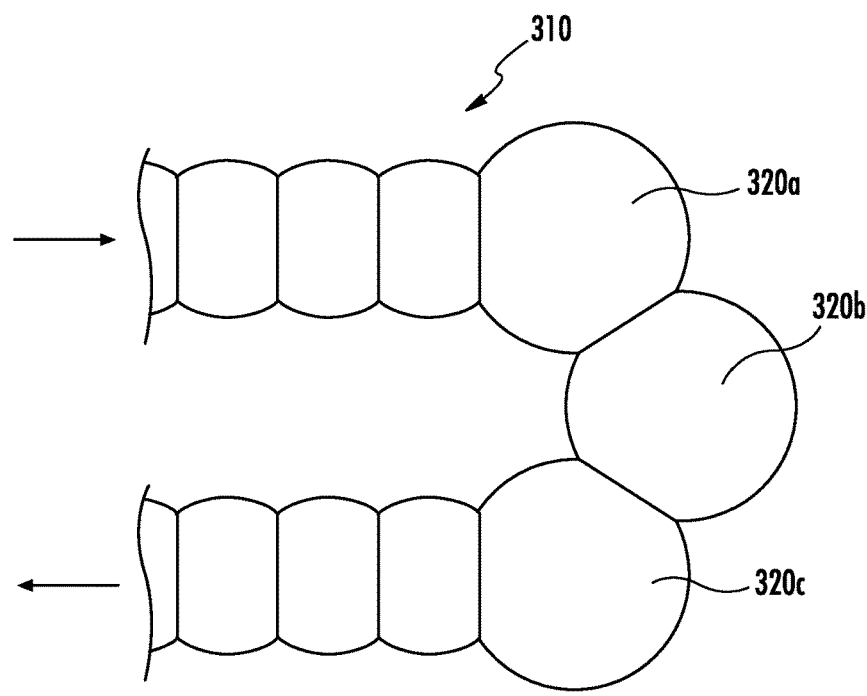
FIG. 12 is a side view of a germicidal chamber in accordance with another exemplary embodiment of the disclosure.
Figure 13:
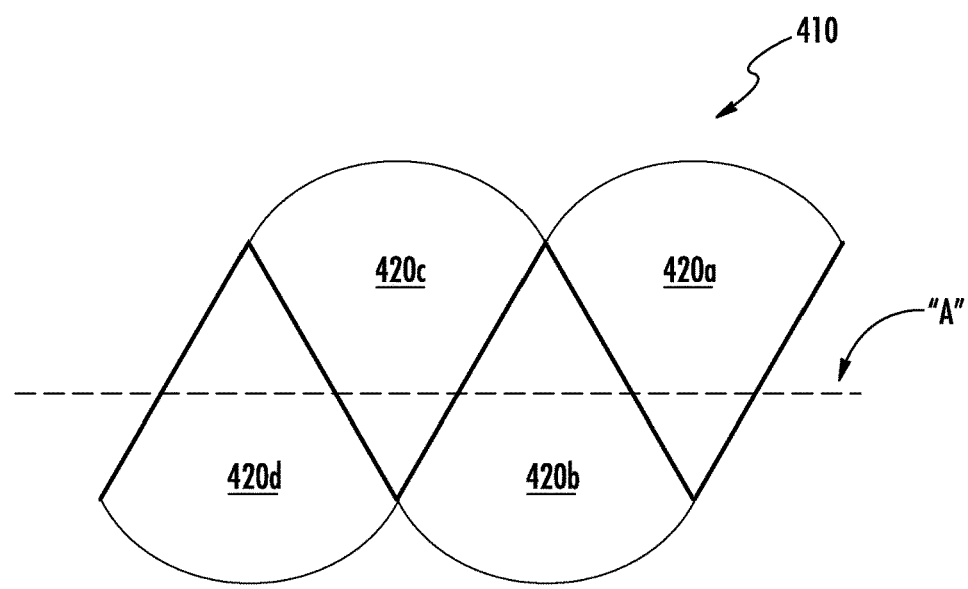
FIG. 13 is a side view of a germicidal chamber in accordance with another exemplary embodiment of the disclosure.

As seen in the exemplary embodiment of FIG. 10, for example, a spherical section 120 truncated in two planes at 90 degrees (one plane at a right angle to axis "A" and one parallel to axis "A") may be employed to allow chamber 110 to achieve a right angle turn. As seen in the exemplary embodiment of FIG. 11, four spherical sections 220a-d truncated in two planes at 90 degrees may be employed to allow chamber 210 to achieve a complete U-turn. Another exemplary embodiment capable of effectuating a complete U-turn is shown in FIG. 12. In this exemplary embodiment, three spherical sections 320a-c truncated in two planes at 60 degrees are employed. A linear chamber 410 is shown in the exemplary embodiment of FIG. 13 provided by joining multiple spherical sections 420a-d truncated in two planes that meet at 60 degrees. Spheres truncated on six sides (not shown) are also contemplated. Such six-sided truncated spheres can be used to form boxes or large cylinders of spheres and would help to increase light incidence and continue to increase steady-state irradiation.

Figure 14A:
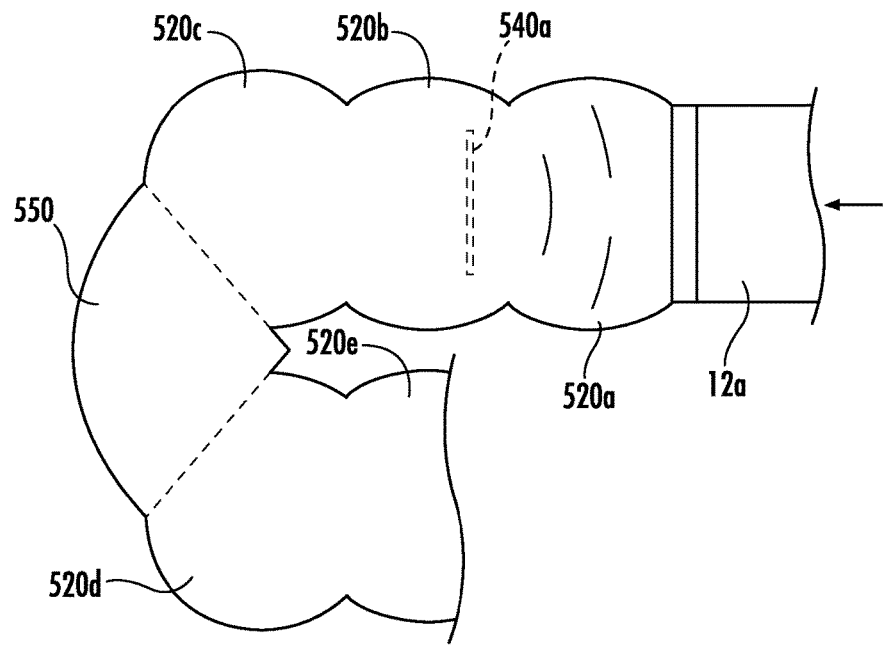
FIGS. 14A and 14B are a side views of germicidal chambers in accordance with other exemplary embodiments of the disclosure that include a non-spherical transition segment.
Figure 14B:
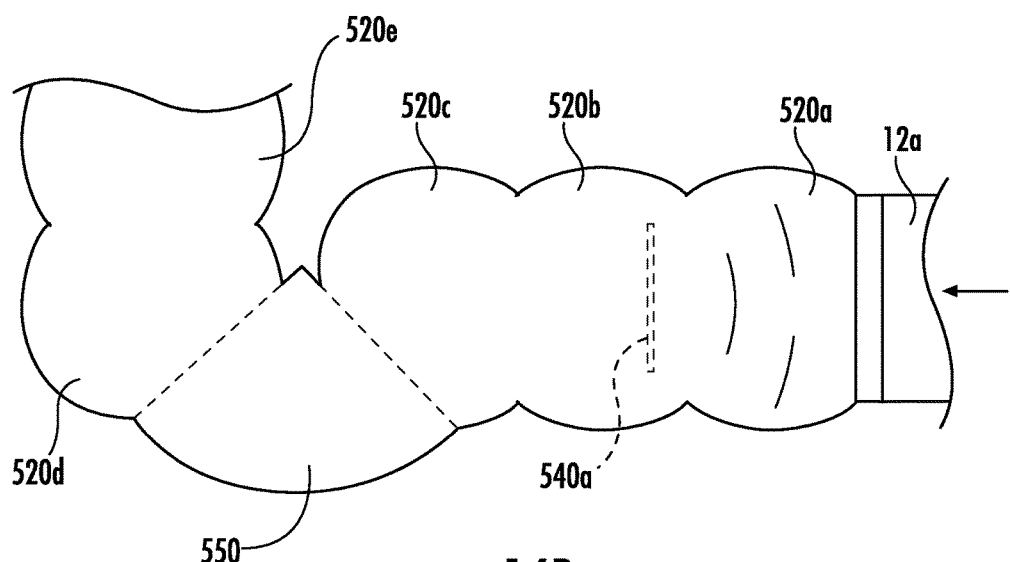

In embodiments, non-spherical segments may be combined with truncated spherical segments to provide a desired configuration. Segment shapes other than a sphere will continue light-energy movement and extend the chamber, so long as an appropriate reflecting material is used on the interior of the segment. As seen in FIG. 14A, for example, segments 520a-520e are truncated spheres, but segment 550 is a transition segment that is non spherical. Re-orientation of the same segments, as shown in the exemplary embodiment of FIG. 14B, results in a different turn in the chamber. Non-spherical segments may permit custom configurations to be achieved, enabling tighter turns in multiple directions with continuous light-energy being applied to the whole volume of the chamber.

Figure 15:
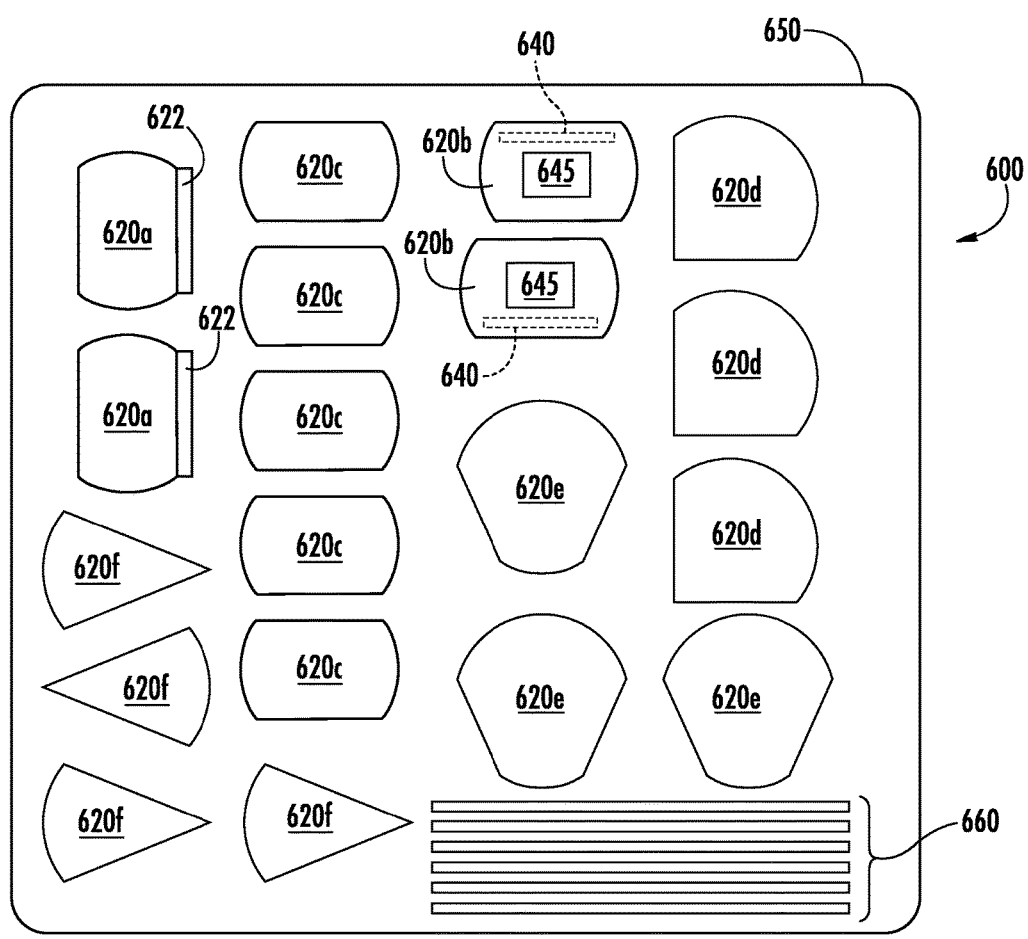
FIG. 15 schematically shows a kit in accordance with an exemplary embodiment of the disclosure.

As noted previously, segments 20a-g may be joined together using any suitable technique. Thus, for example, in embodiments segments 20a-g may include threads at the truncated ends thereof and screw together. It is therefore possible to provide individual components of germicidal chamber as a kit, from which a custom germicidal chamber can be designed and assembled in a desired location. As seen in FIG. 15, for example, an exemplary embodiment of a kit in accordance with an aspect of the present disclosure is shown. Kit 600 has a package 650 that defines a predetermined area that contains a plurality of truncated spherical segments.

The truncated spherical segments contained in the kit may be the same or may be different. For example, kit 600 may include truncated spherical segments 620a that include a collar 622 and thus that may serve as the most upstream and downstream segments of a germicidal chamber. In addition, kit 600 may include truncated spherical segments 620b that include a mounting ring 640 for mounting UV light sources, and an access panel 645. Kit 600 may also include a plurality of truncated spherical segments 620c that are truncated by two parallel planes. Additionally, to allow turns to be made in the germicidal chamber being designed and assembled, kit 600 may include a plurality of truncated spherical segments 620*d* truncated in two planes at 90 degrees, a plurality of truncated spherical segments 620*e* truncated in two planes at 60 degrees, and a plurality of truncated spherical segments 620*f* truncated in two planes that meet at 60 degrees. UV lamps 660 may also be included in kit 600.

While several embodiments have been shown in the drawings, it is not intended that the present disclosure be limited thereto. Persons skilled in the art will understand that the devices and methods specifically described herein and illustrated in the accompanying drawings are non-limiting exemplary embodiments. Various alternatives and modifications can be devised by those skilled in the art based on their reading of the present disclosure. For example, the principles and structures described herein may be used to germicidally treat a liquid by employing a UV transparent conduit passing down the center of the germicidal chamber. Water or other fluids to be germicidally cleansed flow from an inlet pipe through the chamber and out an outlet pipe. The direction of flow can be reversed without affecting the cleansing efficiency. As another example, two chambers running in parallel can be used to provide a backup provision for highly infectious areas, allowing for alternating use during ordinary maintenance, or combined use for a bioterrorism control room or during a terrorist action or accidental environmental release of organic fluids, and the like, always being in operation at all times using a gate or diverter at the inflow end. The present disclosure is intended to embrace all such alternatives, modifications and variances. Also or in addition, the features illustrated or described in connection with one exemplary embodiment may be combined with the features of other embodiments. Such modifications and variations are intended to be included within the scope of the present disclosure. Accordingly, the above description should not be construed as limiting, but merely as exemplifications of embodiments.

What is claimed is:

1. A germicidal chamber comprising:
    a plurality of interconnected truncated spherical segments defining a chamber having a longitudinal axis, an upstream inlet opening, and a downstream outlet opening;
    an ultraviolet light source positioned within the chamber; and
    a grille positioned adjacent the upstream inlet opening, the grille including a plurality of grille elements, each grille element defining a portion of a sphere and having a reflective, concave inner-facing surface that focuses ultraviolet light incident on the grille element to a focal point along the longitudinal axis, the focal point of each of the plurality of grille elements of the grille positioned adjacent the upstream inlet opening being at a different location along the longitudinal axis.

2. The germicidal chamber of claim 1 wherein one or more of the plurality of grille elements of the grille positioned adjacent the upstream inlet opening includes a convex, outer facing surface, at least a portion of the convex, outer facing surface provided with a light absorbing material.

3. The germicidal chamber of claim 1 wherein the reflective, concave inner-facing surface of each grille element of the grille positioned adjacent the upstream inlet opening is a specular reflective surface.

4. The germicidal chamber of claim 3 wherein the reflective, concave inner-facing surface of each grille element of the grille positioned adjacent the downstream outlet opening is a specular reflective surface.

5. The germicidal chamber of claim 3 wherein one or more of the plurality of grille elements of the grille positioned adjacent the downstream outlet opening includes a convex, outer facing surface, at least a portion of the convex, outer facing surface provided with a light absorbing material.

6. The germicidal chamber of claim 1 further comprising a grille positioned adjacent the downstream outlet opening and including a plurality of grille elements, each grille element defining a portion of a sphere and having a reflective, concave inner-facing surface that focuses ultraviolet light incident on the grille element to a focal point along the longitudinal axis, the focal point of each of the plurality of grille elements of the grille positioned adjacent the downstream outlet opening being at a different location along the longitudinal axis.

7. The germicidal chamber of claim 1 wherein at least a portion of the grille is positioned within a squared off shell adjacent the upstream inlet opening.

8. The germicidal chamber of claim 7 further comprising an inner baffle and an outer baffle, the inner and outer baffles positioned within the shell between the grille and the upstream inlet opening.

* * * * *